United States Patent
Harada et al.

(10) Patent No.: US 10,077,282 B2
(45) Date of Patent: Sep. 18, 2018

(54) RAW MATERIAL FOR CHEMICAL DEPOSITION COMPOSED OF ORGANOPLATINUM COMPOUND, AND CHEMICAL DEPOSITION METHOD USING THE RAW MATERIAL FOR CHEMICAL DEPOSITION

(71) Applicant: TANAKA KIKINZOKU KOGYO K.K., Chiyoda-ku, Tokyo (JP)

(72) Inventors: Ryosuke Harada, Tsukuba (JP); Toshiyuki Shigetomi, Tsukuba (JP); Kazuharu Suzuki, Tsukuba (JP); Shunichi Nabeya, Tsukuba (JP); Akiko Kumakura, Tsukuba (JP); Tatsutaka Aoyama, Tsukuba (JP); Takayuki Sone, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 15/558,262

(22) PCT Filed: May 9, 2016

(86) PCT No.: PCT/JP2016/063693
§ 371 (c)(1),
(2) Date: Sep. 14, 2017

(87) PCT Pub. No.: WO2016/181916
PCT Pub. Date: Nov. 17, 2016

(65) Prior Publication Data
US 2018/0072765 A1  Mar. 15, 2018

(30) Foreign Application Priority Data
May 12, 2015 (JP) .................. 2015-096976

(51) Int. Cl.
*H01L 21/31* (2006.01)
*C07F 15/00* (2006.01)
(Continued)

(52) U.S. Cl.
CPC .......... *C07F 15/0086* (2013.01); *C07F 15/00* (2013.01); *C09D 5/24* (2013.01);
(Continued)

(58) Field of Classification Search
CPC ................. C07F 15/0086; C07F 15/00; H01L 21/28568; H01L 21/31; H01L 21/285; C09D 5/24; C23C 16/18
See application file for complete search history.

(56) References Cited

U.S. PATENT DOCUMENTS

| 5,696,384 A | 12/1997 | Ogi et al. |
| 2007/0111025 A1* | 5/2007 | Lennartz ................ C09K 11/06 428/690 |
| 2013/0344243 A1 | 12/2013 | Suzuki et al. |

FOREIGN PATENT DOCUMENTS

| JP | 08-50343 A | 2/1996 |
| JP | 11-292889 A | 10/1999 |

(Continued)

OTHER PUBLICATIONS

International Search Report for PCT/JP2016/063693, dated Jun. 7, 2016.
(Continued)

*Primary Examiner* — Kyoung Lee
(74) *Attorney, Agent, or Firm* — Orrick, Herrington & Sutcliffe LLP; Joseph A. Calvaruso

(57) ABSTRACT

The present invention relates to a raw material for chemical deposition shown in a formulae below and including an organoplatinum compound in which diimine containing two
(Continued)

imines and an alkyl anion are coordinated to divalent platinum. In the formulae, each of substituents $R_1$ to $R_4$ on the diimine represents a hydrogen atom, an alkyl group or the like and has a carbon number of 5 or less. Each of alkyl anions $R_5$ and $R_6$ is an alkyl group having a carbon number of 1 or more and 3 or less. The raw material has high vapor pressure and low decomposition temperature, and thus it is possible to manufacture a platinum thin film at low temperature.

[Chemical Formula 1]

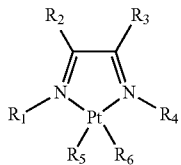

20 Claims, 4 Drawing Sheets

(51) Int. Cl.
C23C 16/18 (2006.01)
H01L 21/285 (2006.01)
C09D 5/24 (2006.01)

(52) U.S. Cl.
CPC ............ *C23C 16/18* (2013.01); *H01L 21/285* (2013.01); *H01L 21/28568* (2013.01); *H01L 21/31* (2013.01)

(56) References Cited

FOREIGN PATENT DOCUMENTS

| | | |
|---|---|---|
| JP | 2001-504159 A | 3/2001 |
| JP | 2009-504911 A | 2/2009 |
| JP | 2013-184925 A | 9/2013 |
| WO | WO 2012/144455 A1 | 10/2012 |

OTHER PUBLICATIONS

Kaim, W. et.al, Reactions of New Organoplatinum(II)and- (IV) Complexes of 1,4-Diaza-1,3-butadienes with Light and Electrons. Emission vs Photochemistry and the Electronic Structures of Ground, Reduced, Oxidized, and Low-Lying Charge-Transfer Excited States, Organometallics, 1998, vol. 17, pp. 237-247.
Klein, A. et al, EPR study of electron transfer and group transfer in organoplatinum(II)and(IV) compounds, J.Chem.Soc.,Perkin Trans. 2, 1997, pp. 2573-2577.
Extended Search Report for EP application No. 16792641.9, dated Feb. 23, 2018.
Takanori et al., "Effects of various deposition conditions on the structure of platinum complex films," Molecular Crystals and Liquid Crystals Science and Technology, Section A: Molecular Crystals and Liquid Crystals, vol. 349, Jan. 1, 2000, pp. 315-318, XP002778088, ISSN: 1058-725X.

\* cited by examiner

250°C

225°C

200°C

RAW MATERIAL FOR CHEMICAL DEPOSITION COMPOSED OF ORGANOPLATINUM COMPOUND, AND CHEMICAL DEPOSITION METHOD USING THE RAW MATERIAL FOR CHEMICAL DEPOSITION

TECHNICAL FIELD

The present invention relates to a raw material for chemical deposition composed of an organoplatinum compound for manufacturing a platinum thin film or a platinum compound thin film by a chemical deposition method, such as a CVD method or an ALD method. In particular, the present invention relates to a raw material for chemical deposition capable of forming a platinum thin film and the like even at low temperature, such as around 200° C., with moderate thermal stability.

BACKGROUND ART

A stereoscopic Ni—Pt silicide electrode having a three-dimensional structure is known as an electrode material of a field-effect transistor (FET) that is built in an integrated circuit. In the manufacturing of the Ni—Pt silicide electrode, a chemical deposition method, such as a CVD method, is utilized when a Pt thin film and a Ni thin film are formed on previously manufactured Si having a steric structure. Further, also in a gate electrode of an FET, a chemical deposition method, such as a CVD method capable of forming a film at low temperature, is suitable in achieving size reduction/high performance.

Many compounds are conventionally known in the past as raw materials for manufacturing a platinum thin film or a platinum compound thin film by the CVD method. For example, bis(acetylacetonate)platinum (II) complex (PTL 1), (cyclopentadienyl)trimethylplatinum (IV)) complex (PTL 2) and the like are mentioned. Required performance of these raw materials for CVD generally include capability of deposition at low temperature because of high vapor pressure and low decomposition temperature.

[Chemical Formula 1]

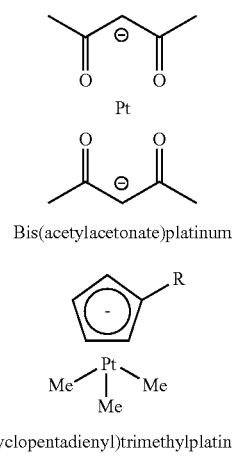

Bis(acetylacetonate)platinum (Cyclopentadienyl)trimethylplatinum

In response to such demand, (1,5-hexadiene)dimethylplatinum (II) or the like is proposed as a compound in which hexadiene (derivative) and an alkyl anion are coordinated to divalent platinum in order to provide a raw material for CVD that is thermally decomposed easily even at low temperature (PTL 3).

[Chemical Formula 2]

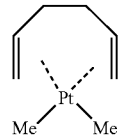

CITATION LIST

Patent Literature

PTL 1: Published Japanese translation of PCT patent application No. 2001-504159
PTL 2: Japanese Patent Laid-Open Heisei No. 11-292889
PTL 3: International Publication No. WO 2012/144455 Pamphlet

SUMMARY OF INVENTION

Technical Problem

Raw materials in the past as described above possess a part of required characteristics for a CVD compound, but do not possess all the required characteristics in a well-balanced manner. For example, platinum compounds in PTL 1 and PTL 2 have high thermal stability but are difficult to deposit at low temperature. The platinum compound in PTL 3 is thermally decomposed easily and excellent in low-temperature film formation properties, but the compound is infrequently decomposed in storage or in vaporization stage before deposition, and there is a room for improvement about thermal stability. As described above, with respect to low-temperature film formation properties in a deposition stage and thermal stability before the deposition stage, such as during storage, when one is possessed, the other is difficult to be realized and there is such a tendency that it is difficult to provide a compound that possesses both characteristics in a well-balanced manner.

Against such a background, the present invention provides a raw material that possesses characteristics required for a CVD compound in a well-balanced manner, that is, a raw material for chemical deposition that enables deposition at low temperature and has sufficient thermal stability without thermal decomposition in a vaporization stage.

Solution to Problem

The present invention that solves the above-described problems relates to a raw material for chemical deposition for manufacturing a platinum thin film or a platinum compound thin film by a chemical deposition method, the raw material including an organoplatinum compound in which diimine containing two imines and an alkyl anion are coordinated to a divalent platinum as shown by a formula below,

[Chemical Formula 3]

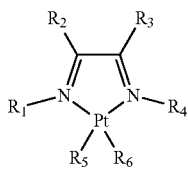

(wherein each of $R_1$ to $R_4$ represents any one of a hydrogen atom, an alkyl group, an alkenyl group, an alkynyl group, an amino group, an imino group, a cyano group and an isocyano group, and has a carbon number of 5 or less. Each of $R_5$ and $R_6$ represents an alkyl group having a carbon number of 1 or more and 3 or less.)

The present inventive raw material for chemical deposition is composed of an organoplatinum compound, in which diimine and two alkyl anions are coordinated as ligands for divalent platinum, as shown below. The present inventors conceived the raw material on the basis of the following reasons with respect to respective constitutions of a central metal and ligands to be coordinated to the metal.

[Chemical Formula 4]

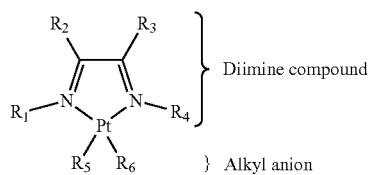

In the present invention, "diimine" means a ligand that has a secondary amine (imine) having a carbon-nitrogen double bond and includes a conjugated diene composed of two conjugated double bonds as a carbon-carbon bond. A central metal and nitrogen in the imine are bonded strongly in the case of a ligand having two secondary amines in this way, and therefore a complex may have higher thermal stability as compared with a case of diene having no nitrogen, as shown below. Further, the diimine can form a complex that is more stable than a complex using a diamine compound not having a conjugated system, depending on the kind and valence number of a central metal. Furthermore, the diimine tends to have a small molecular weight and a low boiling point, evaporates easily after decomposition, and is hard to remain in a metal film as an impurity. A complex having such diimine as a ligand shows easily high vapor pressure.

It is possible for two alkyl anions that are the other ligands to cause a complex to have high vapor pressure by suitably setting molecular weights. Further, these alkyl anions are released as hydrocarbons with a low boiling point by performing deposition in a reducing atmosphere, a hydrogen gas atmosphere and decomposing a complex. Consequently, these alkyl anions are hard to remain as an impurity in a precipitated metal film and are suitable as a ligand for releasing a pure metal.

Furthermore, with respect to platinum to be a central metal, most of platinum complexes with platinum having positive di- or tetra-charges as a central metal are stable, and the present inventors prefer a divalent platinum complex having moderate stability because easy handling of a raw material in the processes of synthesis/purification/storage is also important. On the basis of the above reason, the diimine and an alkyl anion are coordinated as ligands to divalent platinum in the present inventive raw material.

Details of suitable substituents and the like will be described about the above-mentioned platinum ligand.

The diimine contains a hydrogen atom or a group that is any one of an alkyl group, an alkenyl group, an alkynyl group, an amino group, an imino group, a cyano group and an isocyano group and has a carbon number of 5 or less as each of substituents $R_1$ to $R_4$. The application of a comparatively small alkyl group having a carbon number of 5 or less (or a hydrogen atom or the like) as a substituent can suppress the reduction of vapor pressure with the increase in a molecular weight. Vapor pressure tends to decrease when a carbon number is too large and an alkyl group having a carbon number of 6 or more makes it difficult to secure a vapor quantity in film formation and to perform deposition at low temperature in some platinum complexes.

It is preferable that the total carbon number obtained by summing up all carbon numbers of substituents $R_1$ to $R_4$ is 12 or less. A small total carbon number in addition to that each substituent has a comparatively small carbon number can more suppress the decrease in vapor pressure. The total carbon number of substituents $R_1$ to $R_4$ is preferably 2 to 10, and is particularly preferably 4 to 8.

It is preferable for concrete examples of each of substituents $R_1$ and $R_4$ to include any one of a hydrogen atom, a methyl group, an ethyl group, a propyl group and a butyl group, and a propyl group or a butyl group is particularly preferable. Further, any of a linear chain (n-) and branched chains (iso-, sec-, tart-) may be selected when an alkyl group having a carbon number of 3 or more is used. Particularly preferable is an iso-propyl group, a sec-butyl group, a tert-butyl group or the like.

With respect to concrete examples of each of substituents $R_2$ and $R_3$, any one of hydrogen atom and alkyl groups having a carbon number of 3 or less is preferable. A methyl group is suitable as an alkyl group. Further, it is particularly preferable that both $R_2$ and $R_3$ are hydrogen atoms.

Any one of a methyl group, an ethyl group and a propyl group is applied to each of substituents $R_5$ and $R_6$ that are two alkyl anions. As to the propyl group, a linear chain (n-) propyl group is suitable. These alkyl anions have a small molecular weight, and therefore may suppress the reduction of vapor pressure with the increase in a molecular weight when a complex has been formed. Further, stability of a platinum complex tends to decrease as a carbon chain of an alkyl group becomes longer, and it becomes difficult to synthesize/handle a complex having a long chain alkyl group as a ligand. A methyl group is particularly preferable among alkyl groups. A methyl group can be released without leaving an impurity in a metal thin film to be formed because a methyl group becomes a methane having a low boiling point (boiling point: −162° C.) after the decomposition of a complex.

Kinds of organoplatinum compounds that are concretely suitable for the raw material for chemical deposition of the present invention will be exemplified below.

[Chemical Formula 5]

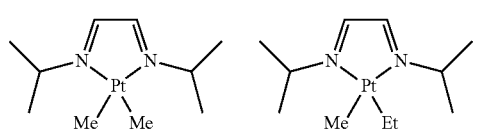

-continued

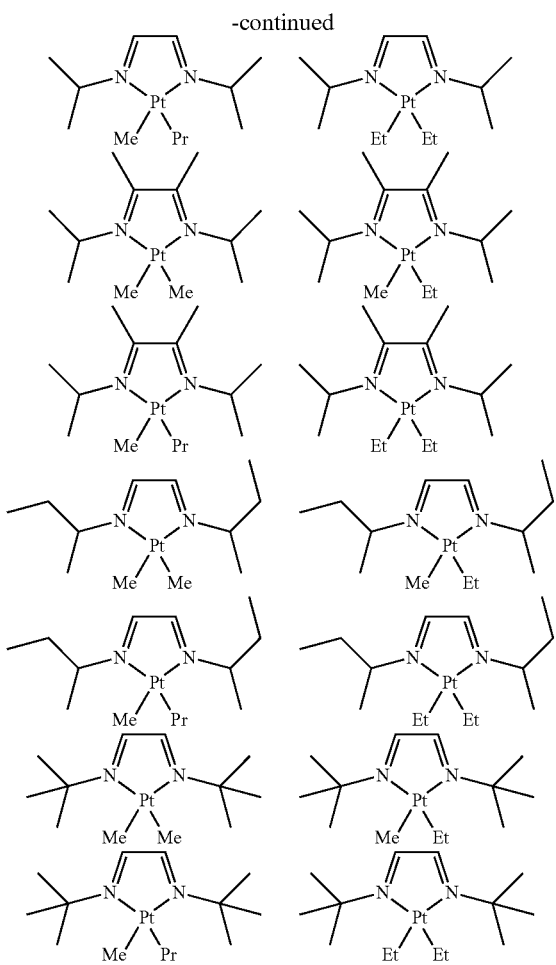

The above-described raw material for chemical deposition of the present invention may be manufactured, using a platinum salt as a starting material, by adding and causing the platinum salt that is the starting material to react with a diimine. Meanwhile, for example, (1,5-hexadiene)dimethylplatinum or the like can be used as a platinum salt.

The present inventive raw material for chemical deposition is useful for forming a platinum thin film by a CVD method. In the method for forming a thin film, a raw material composed of an organoplatinum compound is vaporized to be a reaction gas, the reaction gas is introduced to a substrate surface, and the organoplatinum compound is decomposed to precipitate platinum, in which the present inventive raw material for chemical deposition is used as a raw material.

A reducing atmosphere is preferable as a reaction atmosphere in forming a platinum film. The raw material of the present invention tends to exhibit good low-temperature film formation properties particularly in a reducing atmosphere. Further, a reducing atmosphere also suppresses oxidization of a nickel thin film that is formed together with platinum in a stereoscopic electrode of an FET. As a reducing atmosphere, introduction of hydrogen or ammonia as a reaction gas is preferable, and hydrogen is particularly preferable.

The present invention aims at setting film formation temperature on a low temperature side. From the viewpoint, heating temperature for a deposition reaction is preferably 200° C. to 350° C. Because progress of a deposition reaction is difficult and acquisition of a necessary film thickness is difficult when the heating temperature is less than 200° C.

Further because, when the heating temperature exceeds 350° C., it becomes difficult not only to form a uniform thin film on a stereoscopic electrode but also to maintain performance of an FET element.

Advantageous Effects of Invention

As described above, the platinum complex of the present inventive raw material for chemical deposition has high vapor pressure and low decomposition temperature, and thus it is possible to manufacture a platinum thin film at low temperature. Meanwhile, the present inventive raw material is also applicable to chemical deposition methods, such as an atomic layer deposition method (ALD method), in addition to a CVD method.

DESCRIPTION OF EMBODIMENTS

Figure 1:
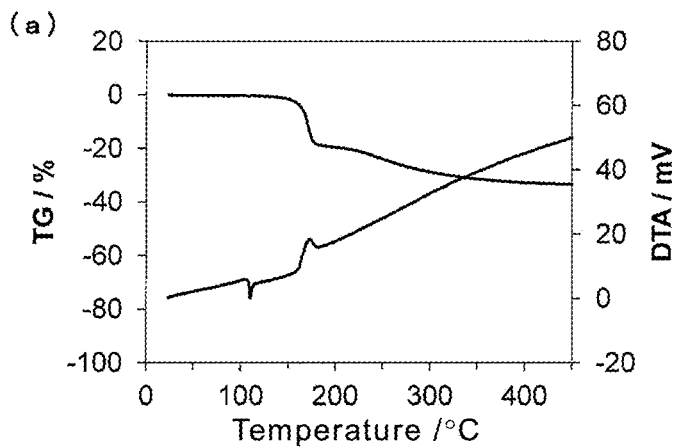
FIG. 1 shows a TG-DTA curve of a platinum complex in a first embodiment.
Figure 1:
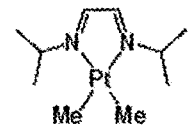
Figure 1:
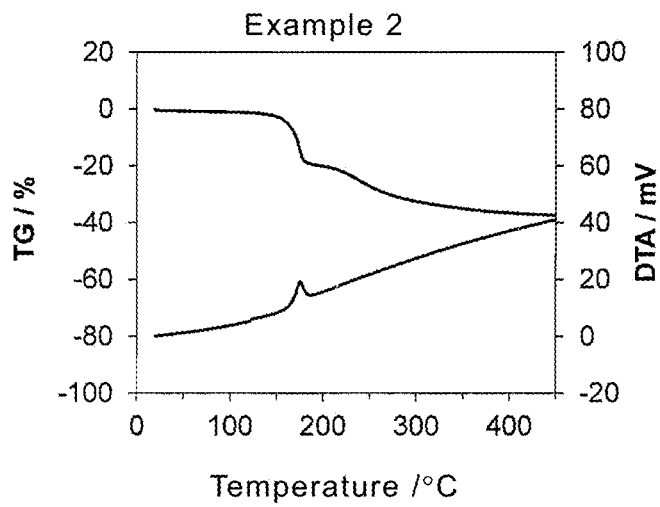
Figure 1:
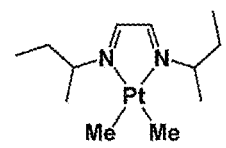
Figure 1:
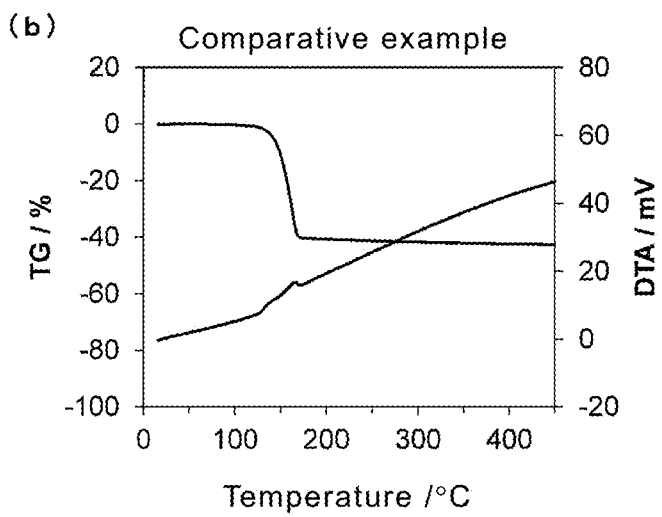
Figure 1:
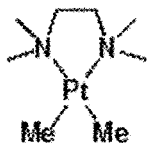

Hereinafter, the best embodiment in the present invention will be described.

First Embodiment

In the present embodiment, three kinds of platinum complexes as described below were synthesized. For the synthesized platinum complexes, physical properties were evaluated and film formation test was performed as a raw material for chemical deposition.

[Chemical Formula 6]

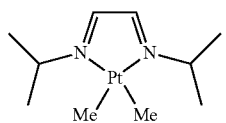

Example 1

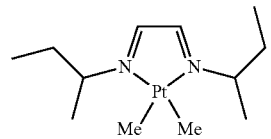

Example 2

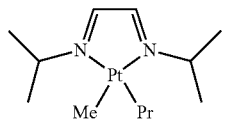

Example 3

Example 1

As a raw material for chemical deposition, there was manufactured a platinum complex: (N,N'-diisopropyl-1,4-diazabutadiene)dimethylplatinum) that was a platinum complex in which diazabutadiene having two iso-propyl groups bonded to two imines and two methyl groups as alkyl anions were coordinated (each of substituents $R_1$ and $R_4$ was an iso-propyl group, each of $R_2$ and $R_3$ was a hydrogen atom, and each of $R_5$ and $R_6$ was a methyl group). The formula of the synthesis reaction is as follows. Hereinafter, the manufacturing process will be described in detail.

[Chemical Formula 7]

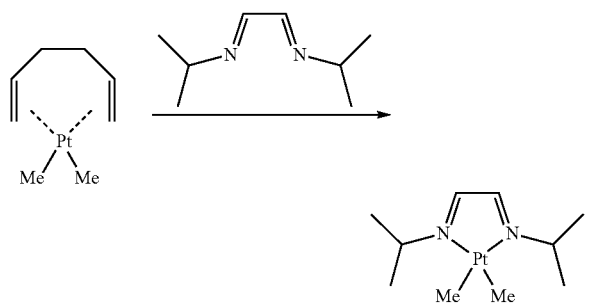

Each of 1.4 g (10 mmol) of N,N'-diisopropyl-1,4-diazabutadiene and 1.55 g (5.0 mmol) of (1,4-hexadiene)dimethylplatinum was added in this order into a flask containing 75 ml of hexane and, after that, the mixture was stirred for 18 hours at room temperature. After the end of the reaction, the reaction product was concentrated to give a magenta solid. The obtained solid was sublimated and purified to give 1.45 g (4.0 mmol) of (N,N'-diisopropyl-1,4-diazabutadiene)dimethylplatinum that was a target (yield: 79%, melting point: 110° C.).

Example 2

As a raw material for chemical deposition, there was manufactured a platinum complex: (N,N'-di-sec-butyl-1,4-diazabutadiene)dimethylplatinum) that was a platinum complex in which diazabutadiene having two sec-butyl groups bonded to two imines and two methyl groups as alkyl anions were coordinated (each of substituents $R_1$ and $R_4$ was a sec-butyl group, each of $R_2$ and $R_3$ was a hydrogen atom, and each of $R_5$ and $R_6$ was a methyl group). The formula of the synthesis reaction is as follows. Hereinafter, the manufacturing process will be described in detail.

[Chemical Formula 8]

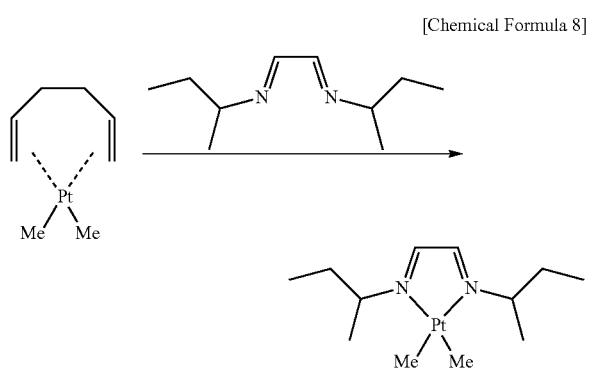

Each of 1.7 g (10 mmol) of N,N'-di-sec-butyl-1,4-diazabutadiene and 1.55 g (5.0 mmol) of (1,4-hexadiene)dimethylplatinum was added in this order into a flask containing 75 ml of hexane and, after that, the mixture was stirred for 18 hours at room temperature. After the reaction was completed, the reaction product was concentrated to give a magenta liquid. The obtained liquid was distilled and purified to give 1.77 g (4.5 mmol) of (N,N'-di-sec-butyl-1,4-diazabutadiene)dimethylplatinum that was a target (yield: 89%).

Example 3

As a raw material for chemical deposition, there was manufactured a platinum complex: (N,N'-diisopropyl-1,4-diazabutadiene)(methyl)(propyl)platinum that was a platinum complex in which diazabutadiene having two iso-propyl groups bonded to two imines and a methyl group and an n-propyl group as alkyl anions were coordinated (each of substituents $R_1$ and $R_4$ was an iso-propyl group, each of $R_2$ and $R_3$ was a hydrogen atom, $R_5$ was a methyl group, and $R_6$ was an n-propyl group). The formula of the synthesis reaction is as follows. Hereinafter, the manufacturing process will be described in detail.

[Chemical Formula 9]

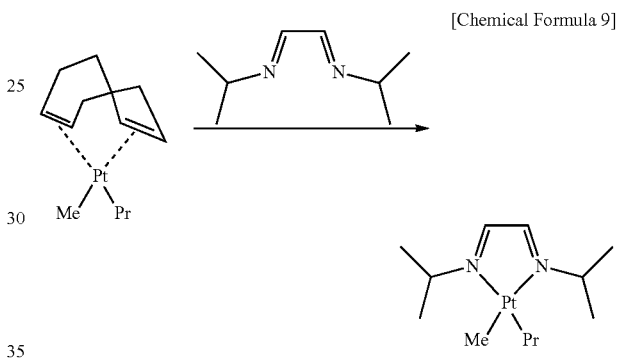

Each of 1.4 g (10 mmol) of N,N'-diisopropyl-1,4-diazabutadiene and 1.81 g (5.0 mmol) of (1,5-cyclooctadiene)(methyl)(propyl)platinum was added in this order into a flask containing 75 ml of hexane and, after that, the mixture was fluxed for 18 hours. After the end of the reaction, the reaction product was concentrated and purified to give 0.2 g (0.5 mmol) of (N,N'-diisopropyl-1,4-diazabutadiene)(methyl)(propyl)platinum that was a target in a state of a magenta liquid (yield: 10%).

Evaluation of Physical Properties of Platinum Complex:

Physical properties of platinum complexes in Examples 1 and 2 were evaluated by TG-DTA. In the analysis, changes in heat quantity and weight of a sample were observed when a platinum complex sample (5 mg) was heated from room temperature to 450° C. that was a range of measurement temperature at a temperature rising rate of 5° C./min under a nitrogen atmosphere with TG-DTA2000SA manufactured by BRUKER Corporation. Results are shown in FIG. 1(a). Further, there are shown results of TG-DTA analysis that was performed in the same way as above using dimethyl (N,N,N',N'-tetramethylethylenediamine)platinum not having conjugated diene as Comparative Example (FIG. 1(b)).

From the results of DTA in FIG. 1, there was seen from (a) a build up of an exothermic peak that was convex upward near 160° C. in complexes in Examples 1 and 2 in which the diimine was coordinated. In contrast, there was seen from (b) a build up of an exothermic peak near 125° C. in a complex in which diamine was coordinated. The exothermic peak suggests generation of decomposition of a compound. Accordingly, the complexes in Examples 1 and 2 (diimine was coordinated) had a decomposition temperature that was higher in around 35° C. and had a higher thermal stability as compared with the complex in which diamine was coordinated. From the viewpoint, the compound in Comparative Example decomposes and cannot be purified when a sublimation experiment (30 Pa, 110 to 120° C.) is performed but, in contrast, the compound in Example 1 is not decomposed and can be purified. Meanwhile, a difference occurs between results of the sublimation experiment and the evaluation by TG-DTA because conditions such as presence/absence of measurement temperature rising are different.

Film Formation Test:

Next, film formation tests of platinum thin films were performed by a CVD method with platinum complexes in Examples 1 to 3 used as raw compounds.

Figure 2:
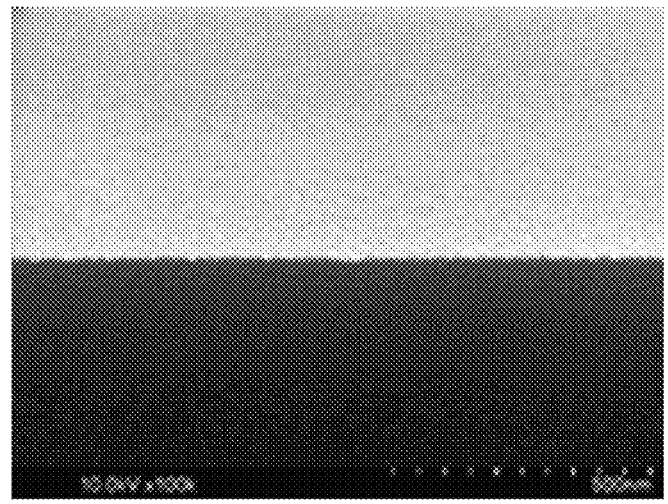
FIG. 2 shows a cross-sectional photograph of a platinum thin film in the first embodiment.

A platinum thin film was deposited on a silicon substrate (15 mm×15 mm). A thermal CVD apparatus of a hot wall type was used as a deposition apparatus. A reaction gas (hydrogen) was flown at a constant flow rate using a mass flow controller. Film formation conditions are as follows. Further, specific resistance of the thin film was measured by a four-probe method. The result of SEM observation of the formed platinum thin film is shown in FIG. 2.

Substrate: Si
Film formation temperature: 250° C.
Sample temperature: 105° C.
Film formation pressure: 5 torr
Flow rate of reaction gas (hydrogen): 10 sccm
Film formation time: 10 minutes As the results of the above film formation tests, the platinum thin film was able to be deposited and the formed thin film had a smooth and uniform surface in all cases where any complex in Examples 1 to 3 was used as a raw material. Film thickness and specific resistance were measured for the platinum thin film that was formed in Example 1, and the Pt film had a sufficient thickness of 6.5 nm and a low specific resistance of 77.2 µΩ·cm. Further, the formation of a platinum thin film having a smooth and uniform surface was confirmed also by the SEM photograph in FIG. 2.

Second Embodiment

In the present embodiment, film formation tests onto respective Si substrates in the first embodiment were performed at film formation temperatures of 200° C. and 225° C. to evaluate low-temperature film formation properties. Other film formation conditions were the same as the conditions in the first embodiment. Results are shown in Table below. The deposition results in the first embodiment are shown together in the Table below. Further, a SEM-observed result of the formed platinum thin film is shown in FIG. 3.

TABLE 1

| Film formation temperature (° C.) | Pt film thickness (nm) | Specific resistance (µΩ · cm) |
| --- | --- | --- |
| 200 | 4.5 | 85.8 |
| 225 | 6.5 | 97.8 |
| 250 | 6.5 | 77.2 |

Figure 3:
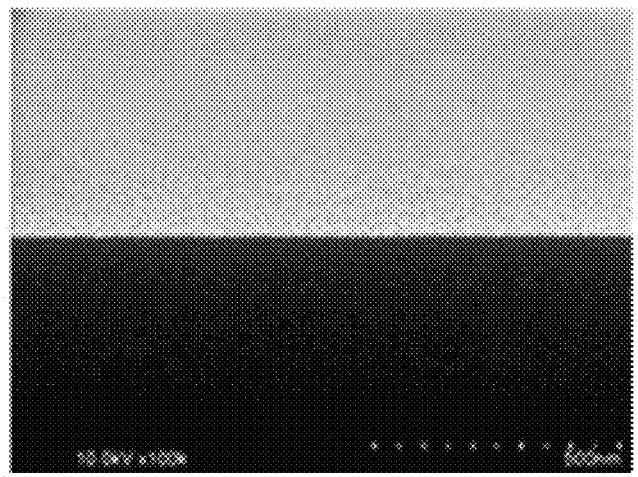
FIG. 3 shows a cross-sectional photograph of a platinum thin film in a second embodiment.
Figure 3:
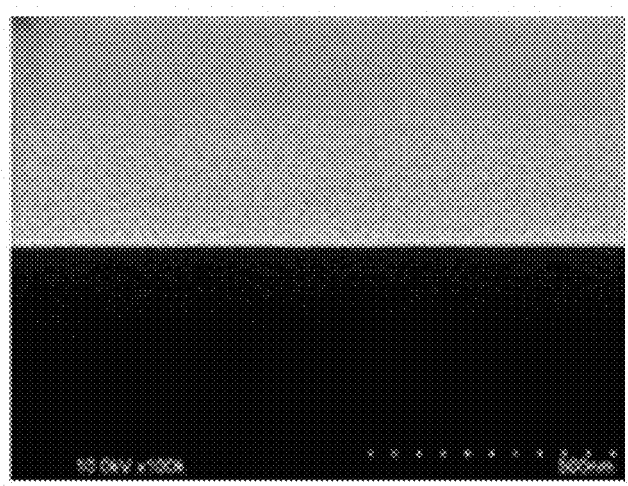

Platinum thin films that were formed at 200° C. or 225° C. in film formation temperature also had a smooth and uniform surface from SEM photographs in FIG. 3. Further, the Pt film thickness and the specific resistance were almost equivalent to those in the case when a film was formed at 250° C. in film formation temperature as shown in above Table.

Third Embodiment

In the present embodiment, dimethyl(N,N,N',N'-tetramethylethylenediamine)platinum was used as Comparative Example relative to Example and thermal stability and deposition properties were evaluated.

Reduced Pressure TG Measurement (Vaporization Properties):

A platinum complex sample (5 mg) was heated and analyzed with TG-DTA2000SA manufactured by BRUKER Corporation in a measurement temperature range of room temperature to 450° C. at temperature rising rate of 5° C./min and pressure of 5 torr under a nitrogen atmosphere. Results are shown in FIG. 4.

Figure 4:
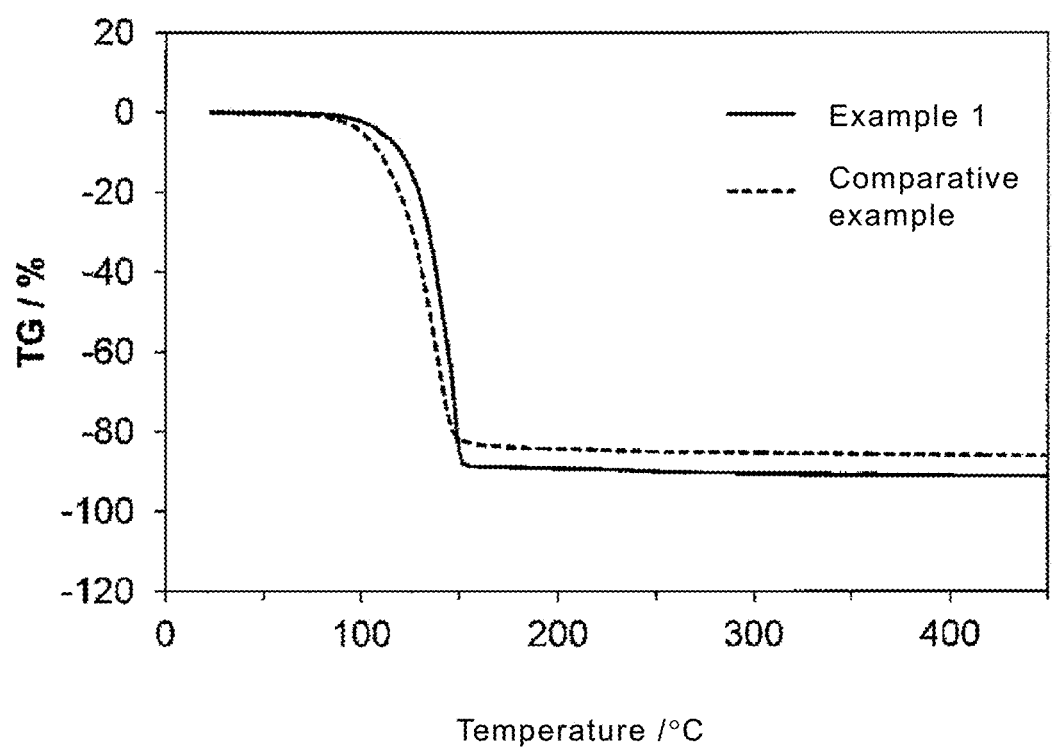
FIG. 4 shows a TG curve of a platinum complex in a third embodiment.

From the result of TG measurement, it was shown that the complex having diamine in Comparative Example generated about 15% of residue, and that the complex having the diimine in Example 1 generated around 10% of residue and had high thermal stability and high sublimation efficiency irrespective of high vaporization initiation temperature, from FIG. 4. It is considered that the complex having diamine in Comparative Example had low vapor pressure and generated thermal decomposition prior to vaporization in the temperature rising process.

Film Formation Test:

A Pt thin film was formed on a substrate Si at 200° C. in film formation temperature using the platinum complex in Example or in Comparative Example as a raw material for chemical deposition. In Comparative Example, sample temperature was set to be 110° C. Other film formation conditions were set to be the same as conditions in the first embodiment.

As the results of film formation tests, a platinum thin film was formed even at 200° C. in film formation temperature in the case of the complex in Example 1 but, in contrast, a film was not able to be formed in the case of the complex in Comparative Example because decomposition of the compound occurred in vaporization of the sample.

From the above, it was confirmed that the complex in Example 1 had both vaporization properties and film formation properties suitable for the formation of a platinum thin film.

INDUSTRIAL APPLICABILITY

The present inventive raw material has high vapor pressure and is capable of forming a highly accurate platinum thin film at low temperature and also has moderate thermal stability to exert excellent handling properties. Consequently, the raw material is useful for the film formation onto a steric structure and can be applied to a stereoscopic electrode having a three-dimensional structure of a field-effect transistor (FET), and the like.

The invention claimed is:

1. A raw material for chemical deposition for manufacturing a platinum thin film or a platinum compound thin film by a chemical deposition method, the raw material comprising an organoplatinum compound in which diimine containing two imines and alkyl anions are coordinated to a divalent platinum as shown by a formula below:

[Chemical Formula 1]

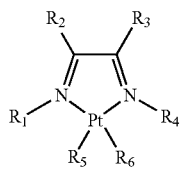

(wherein, each of $R_1$ to $R_4$ represents any one of a hydrogen atom, an alkyl group, an alkenyl group, an alkynyl group, an amino group, an imino group, a cyano group and an isocyano group and each has a carbon number of 5 or less; and each of $R_5$ and $R_6$ represents an alkyl group having a carbon number of 1 or more and 3 or less).

2. The raw material for chemical deposition according to claim 1, wherein each of $R_1$ and $R_4$ represents any one of a hydrogen atom, a methyl group, an ethyl group, a propyl group and a butyl group.

3. The raw material for chemical deposition according to claim 1, wherein each of $R_1$ and $R_4$ represents any one of an iso-propyl group, a sec-butyl group and a tert-butyl group.

4. The raw material for chemical deposition according to claim 1, wherein each of $R_2$ and $R_3$ represents a hydrogen atom or a methyl group.

5. The raw material for chemical deposition according to claim 1, wherein a total carbon number obtained by summing up all carbon numbers of substituents $R_1$ to $R_4$ is 12 or less.

6. The raw material for chemical deposition according to claim 1, wherein each of $R_5$ and $R_6$ represents any one of a methyl group, an ethyl group and an n-propyl group.

7. A chemical deposition method of a platinum thin film or a platinum compound thin film, comprising: vaporizing a raw material composed of an organoplatinum compound to form a raw material gas, and heating the raw material gas while introducing the raw material gas onto a substrate surface,
wherein the raw material for chemical deposition defined in claim 1 is used as the raw material.

8. The raw material for chemical deposition according to claim 2, wherein each of $R_1$ and $R_4$ represents any one of an iso-propyl group, a sec-butyl group and a tert-butyl group.

9. The raw material for chemical deposition according to claim 2, wherein each of $R_2$ and $R_3$ represents a hydrogen atom or a methyl group.

10. The raw material for chemical deposition according to claim 3, wherein each of $R_2$ and $R_3$ represents a hydrogen atom or a methyl group.

11. The raw material for chemical deposition according to claim 2, wherein a total carbon number obtained by summing up all carbon numbers of substituents $R_1$ to $R_4$ is 12 or less.

12. The raw material for chemical deposition according to claim 3, wherein a total carbon number obtained by summing up all carbon numbers of substituents $R_1$ to $R_4$ is 12 or less.

13. The raw material for chemical deposition according to claim 4, wherein a total carbon number obtained by summing up all carbon numbers of substituents $R_1$ to $R_4$ is 12 or less.

14. The raw material for chemical deposition according to claim 2, wherein each of $R_5$ and $R_6$ represents any one of a methyl group, an ethyl group and an n-propyl group.

15. The raw material for chemical deposition according to claim 3, wherein each of $R_5$ and $R_6$ represents any one of a methyl group, an ethyl group and an n-propyl group.

16. The raw material for chemical deposition according to claim 4, wherein each of $R_5$ and $R_6$ represents any one of a methyl group, an ethyl group and an n-propyl group.

17. The raw material for chemical deposition according to claim 5, wherein each of $R_5$ and $R_6$ represents any one of a methyl group, an ethyl group and an n-propyl group.

18. A chemical deposition method of a platinum thin film or a platinum compound thin film, comprising: vaporizing a raw material composed of an organoplatinum compound to form a raw material gas, and heating the raw material gas while introducing the raw material gas onto a substrate surface,
wherein the raw material for chemical deposition defined in claim 2 is used as the raw material.

19. A chemical deposition method of a platinum thin film or a platinum compound thin film, comprising: vaporizing a raw material composed of an organoplatinum compound to form a raw material gas, and heating the raw material gas while introducing the raw material gas onto a substrate surface,
wherein the raw material for chemical deposition defined in claim 3 is used as the raw material.

20. A chemical deposition method of a platinum thin film or a platinum compound thin film, comprising: vaporizing a raw material composed of an organoplatinum compound to form a raw material gas, and heating the raw material gas while introducing the raw material gas onto a substrate surface,
wherein the raw material for chemical deposition defined in claim 4 is used as the raw material.

* * * * *